US007892490B2

(12) United States Patent
Oh et al.

(10) Patent No.: US 7,892,490 B2
(45) Date of Patent: Feb. 22, 2011

(54) SEMIAUTOMATIC OPERATING DEVICE FOR MICROCHIP

(75) Inventors: Kwang-wook Oh, Hwaseong-si (KR); Yu-jin Seo, Daejeon-si (KR)

(73) Assignee: Samsung Electronics Co., Ltd. (KR)

( * ) Notice: Subject to any disclaimer, the term of this patent is extended or adjusted under 35 U.S.C. 154(b) by 988 days.

(21) Appl. No.: 11/391,850

(22) Filed: Mar. 29, 2006

(65) Prior Publication Data

US 2006/0246487 A1 Nov. 2, 2006

(30) Foreign Application Priority Data

Mar. 29, 2005 (KR) ...................... 10-2005-0025974

(51) Int. Cl.
*G01N 21/00* (2006.01)
*G01N 31/00* (2006.01)
*C12M 1/36* (2006.01)
*C12M 1/38* (2006.01)

(52) U.S. Cl. ........................... 422/63; 422/99; 422/104; 422/243; 422/297; 422/300; 422/302; 435/286.2; 435/287.3; 435/288.1; 435/288.3; 435/305.1; 435/305.4; 251/318; 251/319

(58) Field of Classification Search .................. 422/63, 422/99, 104, 243, 297, 300, 302; 435/286.2, 435/287.3, 288.1, 288.3, 305.1, 305.4; 251/318, 251/319
See application file for complete search history.

(56) References Cited

U.S. PATENT DOCUMENTS

| | | | | | |
|---|---|---|---|---|---|
| 5,207,666 | A * | 5/1993 | Idriss et al. | .............. | 604/891.1 |
| 6,140,044 | A * | 10/2000 | Besemer et al. | ................ | 435/6 |
| 6,145,702 | A * | 11/2000 | Lin et al. | ...................... | 222/64 |
| 6,964,862 | B2 * | 11/2005 | Chen | ......................... | 435/91.2 |
| 2002/0037237 | A1 * | 3/2002 | Mainquist et al. | ............. | 422/63 |
| 2003/0015682 | A1 * | 1/2003 | Killeen et al. | ............... | 251/368 |
| 2010/0038576 | A1 * | 2/2010 | Hunnicutt | ................... | 251/318 |

FOREIGN PATENT DOCUMENTS

| | | | |
|---|---|---|---|
| KR | 10-2006-0031073 | | 4/2006 |
| WO | WO-9621142 | * | 7/1996 |

* cited by examiner

*Primary Examiner*—Nathan A Bowers
(74) *Attorney, Agent, or Firm*—Cantor Colburn LLP

(57) ABSTRACT

Provided is an apparatus for performing a chemical reaction using a microchip having at least one micro-channel. The device, which is a semiautomatic operating device for a microchip on which at least one micro-channel with a reagent inlet is formed, includes: a base which accommodates the microchip; a slider with injection inlets corresponding to the reagent inlets that reciprocally move parallel to the base; and a slider moving unit which selectively moves the slider to a first location at which the microchip is opened, after the injection inlet of the slider and the reagent inlet are aligned, and to a second location where the microchip is sealed by a bottom surface of the slider covering the reagent inlet.

6 Claims, 8 Drawing Sheets

SEMIAUTOMATIC OPERATING DEVICE FOR MICROCHIP

This application claims the priority of Korean Patent Application No. 10-2005-0025974, filed on Mar. 9, 2005 in the Korean Intellectual Property Office, the disclosure of which is incorporated herein in its entirety by reference.

BACKGROUND OF THE INVENTION

1. Field of the Invention

The present invention relates to a semiautomatic operating device for a microchip having at least one micro-channel capable of making the performance of biochemical reaction experiments using the microchip easier.

2. Description of the Related Art

Conventional micro-channels and microchips including chambers in which a biochemical reaction can occur are well known. An example of a microchip is a polymerase chain reaction (PCR) chip in which a micro-channel and a reaction chamber are formed. In conventional microchips, injection equipment such as a pipette is used to inject reaction reagents directly into a reagent inlet of the microchip. However, when a multi-channel PCR chip having a plurality of reaction chambers is used, such a manual operation can cause a large error due to confusing channels of the PCR or shaking of the hands.

In addition, the microchip must be sealed after a PCR reagent is injected so that the PCR reagent is not lost by, for example, evaporation while a PCR is performed. An example of a conventional method of sealing the microchip is adhering an optical tape to the reagent inlet and outlet of the PCR chip. In this case, a conventional reaction experiment using the microchip is inconvenient since the PCR reagent must be manually injected and the reagent inlet and outlet sealed using a separately prepared sealing material such as tape.

Therefore, a semiautomatic operating device for a microchip in which a reaction solution can be simply and accurately injected and a reagent inlet and outlet can be easily sealed after injecting the reaction solution by a simple manipulation of the device regardless of the level of the skill of a user is required.

SUMMARY OF THE INVENTION

The present invention provides a microchip unit which opens a reagent inlet of a micro-channel, guides a pipette tip that injects a reaction solution into the reagent inlet, and includes a slider which seals the reagent inlet and an outlet of the micro-channel after the injection, and a semiautomatic operating device for the microchip unit which can slide the slider to an injection location or a sealing location through a simple manipulation.

According to an aspect of the present invention, there is provided a semiautomatic operating device for a microchip on which at least one micro-channel with a reagent inlet is formed. The semiautomatic operating device includes: a base which accommodates the microchip; a slider with injection inlets corresponding to the reagent inlets that reciprocally move parallel to the base; and a slider moving unit which selectively moves the slider to a first location at which the microchip is opened, after the injection inlet of the slider and the reagent inlet are aligned, and to a second location where the microchip is sealed by a bottom surface of the slider covering the reagent inlet.

Hereinafter, the base accommodating the microchip and a portion including the slider will be referred as a "microchip unit" for convenience. The microchip unit is disclosed in more detail in Korean Patent Application No. 2004-0079957 filed by the present applicant prior to the filing of the present application, and the present invention provides the microchip unit and the semiautomatic operating device for a microchip, which accurately moves the slider of the microchip to the first and second locations through a simple manipulation.

The term "microchip" used throughout the specification includes a micro-channel and a chamber that is connected to the micro-channel and can be opened and closed from the micro-channel. The microchip can perform various chemical reactions in the chamber using a small amount of a reaction solution. Such a microchip is well known to those skilled in the prior art related to the present invention. An example of the microchip is a PCR chip in which a micro-channel and a reaction chamber that can be connected to the micro-channel are formed.

The PCR chip used in the present invention as an example of the microchip is well known to those skilled in the prior art related to the present invention. Generally, a "PCR chip" refers to a device including a micro-channel and a micro chamber in which a micro PCR can be performed. The PCR chip may be a single PCR chip having a single channel and chamber, or a multi-channel PCR chip having a plurality of channels and chambers.

Throughout the specification, "PCR," an acronym for a polymerase chain reaction, is a process in which a target nucleotide is amplified from a pair of primers specifically binded to the target nucleotide using the polymerase. In PCR, an enzyme related polymerization, a primer, a template, and a solution including other subsidiary elements (a.k.a. "PCR mixture") are injected into a chamber. Then, the contents of the chamber are maintained at an annealing temperature at which the primer and the template are annealed, a polymerizating temperature at which polymerization occurs by the polymerase, and a denaturizing temperature at which the polymerized double strands are denatured into single strands for a predetermined periods of time. A target nucleotide is amplified by repeating the temperature cycle mentioned above. PCR is also known as thermal cycling reaction. The PCR chip used in the present invention may represent every sort of PCR chips ever known in the art.

According to the present invention, an accommodating unit for accommodating the microchip and slider guides which allow the sliders to slide parallel to the base are formed on the base. Any fixing element may fix the base and the microchip. The slider guides on the base and the sliders may be connected by grooves in the shape of horizontal straight lines and protrusions in the shape of horizontal straight lines corresponding to the grooves so that the sliders can slide.

According to the present invention, the sliders have injection inlets corresponding to each of the reagent inlets of the microchip. The bottom surfaces of the sliders adjacent to the injection inlets are formed to be able to open or close the reagent inlets. The sliders may include a pressurizing sealing element to maintain inside the microchip airtight while the reagent inlets are closed. The sliders cannot slide perpendicular to the base by being guided by the slider guides of the base, they can slide between first and second locations in a parallel direction to the base.

The first location is where the injection inlets are aligned with each of the reagent inlets of the microchip to open the microchip. The second location is where the pressurizing sealing element seals the reagent inlets and outlets of the microchip to close the microchip. The pressurizing sealing element may be made of any material having elasticity and little reaction, and is not limited to a specific material. However, the pressurizing sealing element may be made of rubber or PDMS, and may be made of PDMS.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

Figure 1:
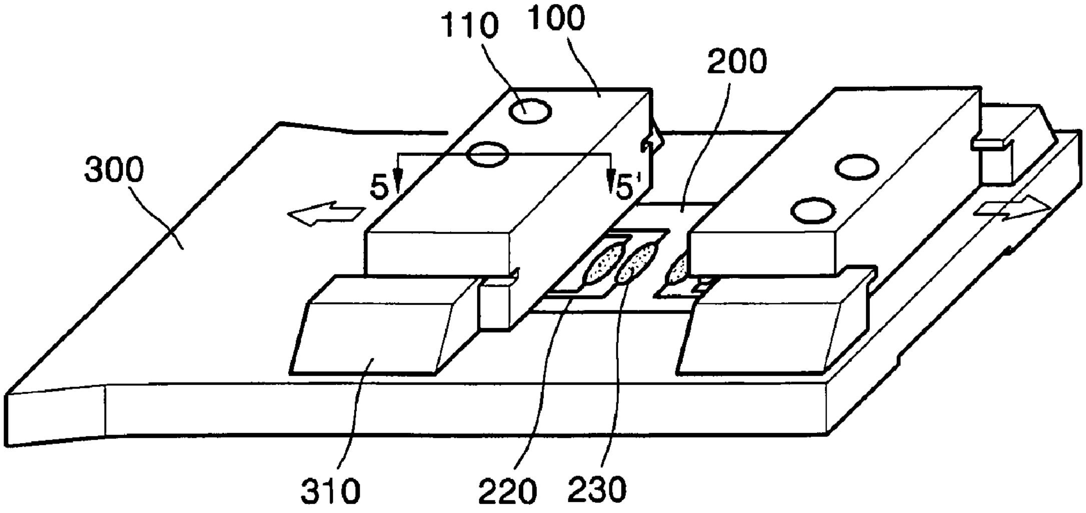
FIG. 1 is a perspective view of a polymerase chain reaction (PCR) chip unit including two sliders disposed at a first location according to an embodiment of the present invention.

The present invention will now be described more fully with reference to the accompanying drawings, in which exemplary embodiments of the invention are shown. Like reference numerals in the drawings denote like elements.

FIG. 1 is a perspective view of a polymerase chain reaction (PCR) chip unit including two sliders 100 disposed at a first location according to an embodiment of the present invention. Referring to FIG. 1, a micro-channel 220 and a micro chamber 230 are formed on a PCR chip 200, and thus PCR can be performed by a heat supplying element. The PCR chip 200 is accommodated on a base 300 on which slider guides 310 are formed. Injection inlets 110 are formed on the sliders 100, and the sliders 100 are guided by the slider guides 310 to slide parallel to the PCR chip 200 and the base 300. The injection inlets 110 are aligned with reagent inlets 210 (see FIG. 3) of the PCR chip 200 when the sliders 100 are disposed at the first location. As a result, a PCR reagent can be injected into the micro-channel 220 and the chamber 230 of the PCR chip 200 via the injection inlet 110 using an injection device such as a pipette. As an example, in FIG. 1, the sliders 100 have grooves in the shape of horizontal straight lines on both sides thereof and the slider guides 310 have protrusions in the shape of horizontal straight lines corresponding to the grooves formed on the slider 100, and the sliders 100 and the slider guides 310 are coupled to each other by meshing. The sliding guides 310 may have any other structures as long as the sliders 100 are fixed in the vertical direction and enables the slider 100 to slide in the horizontal direction.

Figure 2:
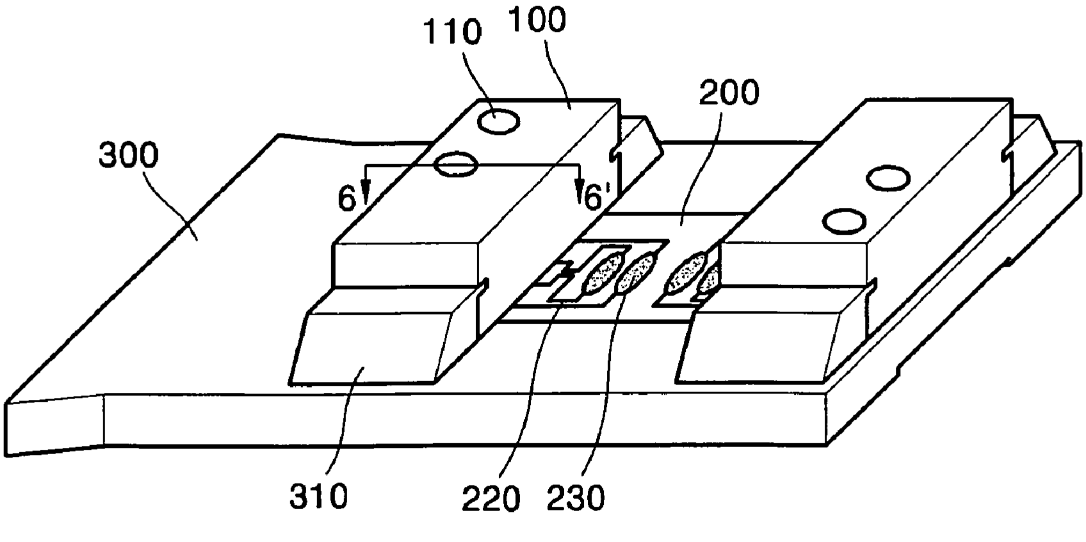
FIG. 2 is a perspective view of the PCR chip unit of FIG. 1 when the sliders are disposed in a second location.

FIG. 2 is a perspective view of the PCR chip unit of FIG. 1 when the two sliders 100 are disposed in a second location. When the sliders 100 are located at the first location in FIG. 1 and slide in directions indicated by arrows illustrated in FIG. 1 by applying a force to the sliders 100, the sliders 100 move to the second location illustrated in FIG. 2. By sliding the sliders 100 from the first location to the second location, pressurizing sealing elements 120 (see FIG. 4) formed on bottom surfaces of the sliders 100 seal the reagent inlets 210 and outlets of the PCR chip 200. The reagent inlets 210 sealed in this way experience pressure in the vertical direction, and are thus sealed by the pressurizing sealing elements 120. Consequently, leakage of a PCR reaction solution during a PCR reaction is prevented.

Figure 3:
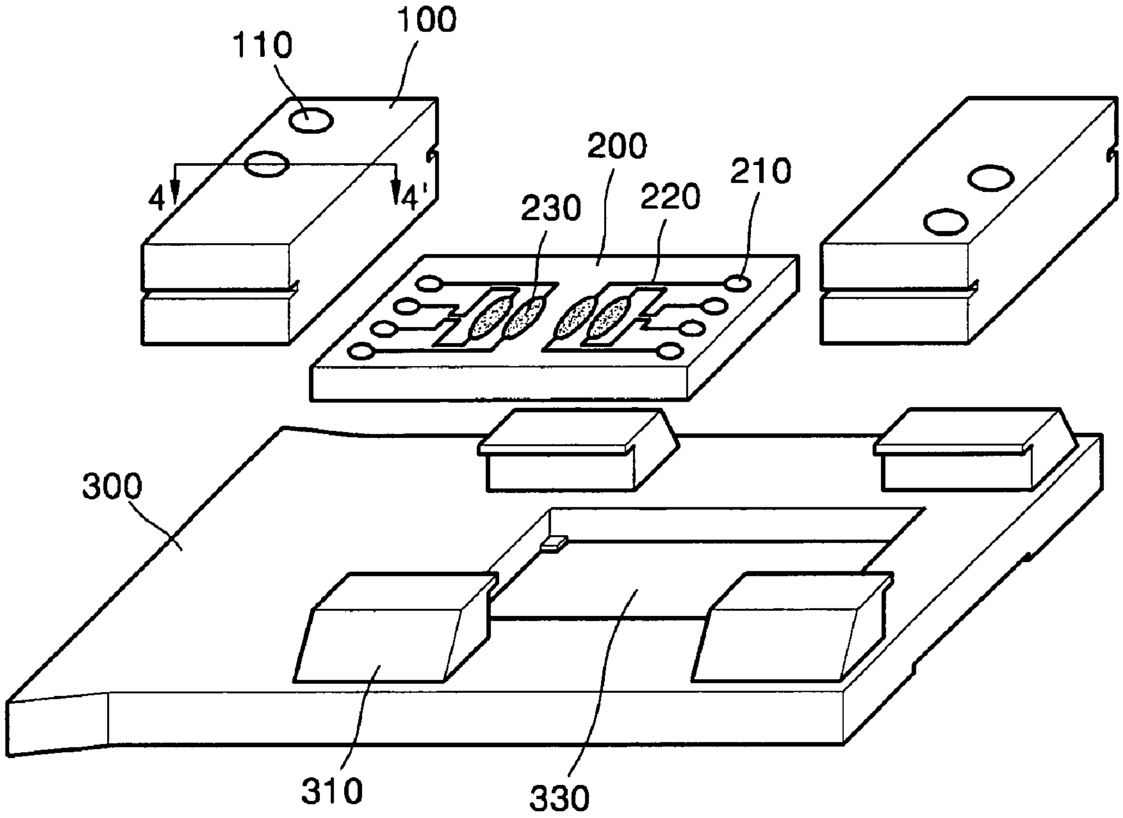
FIG. 3 is an exploded perspective view of the PCR chip unit illustrated in FIGS. 1 and 2.

FIG. 3 is an exploded perspective view of the PCR chip unit illustrated in FIGS. 1 and 2. Referring to FIG. 3, the PCR chip is composed of the two sliders 100, the multi-channel PCR chip 200, and the base 300. The multi-channel PCR chip 200 is horizontally fixed to a PCR chip accommodating unit 330 of the base 300 on which the sliders guides 310 are formed. The PCR chip 200 comprises the reagent inlets 210 and outlets into which a PCR mixture or a reaction product is injected or output, the micro-channels 220, and the chambers 230, and these components are connected to one another. The sliders 100 are installed on the slider guides 310 after the PCR chip 200 is fixed to the base 300. The sliders 100 are fixed in the vertical direction and are guided to slide in the horizontal direction from the first location to the second location and vice versa.

Figure 4:
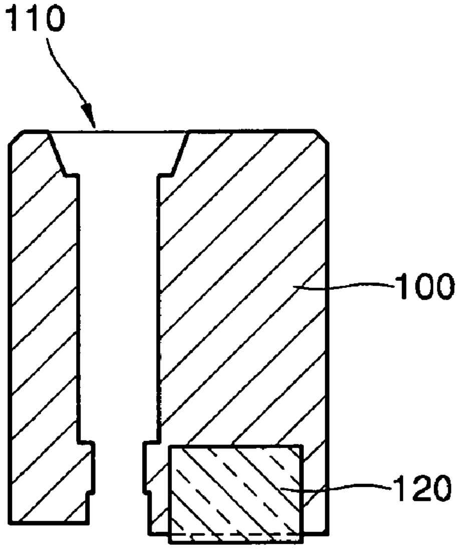
FIG. 4 is a cross-section of the slider in FIG. 3 taken along the line 4-4'.

FIG. 4 is a cross-section of the slider 100 in FIG. 3 taken along the line 4-4'. Referring to FIG. 4, the injection inlet 110 is formed in the slider 100, and a lower portion of the injection inlet 110 is aligned with the reagent inlet 210 of the PCR chip 200 when the slider 100 is at the first location, thereby allowing the PCR reagent to freely flow into the reagent inlet 210. Therefore, when the slider 100 is disposed in the first location, the PCR reagent can be injected into the channels 220 and the chambers 230 of the PCR chip 200 by injecting the PCR reagent into the injection inlet 110 using an injection device such as a pipette. The pressurizing sealing element 120 such as a PDMS or rubber may be formed on the bottom surface of the slider 100. The pressurizing sealing element 120 may protrude from the bottom surface of the slider 100 so that a predetermined pressure can be applied to the reagent inlets 210 and outlets in a downward direction.

Figure 5:
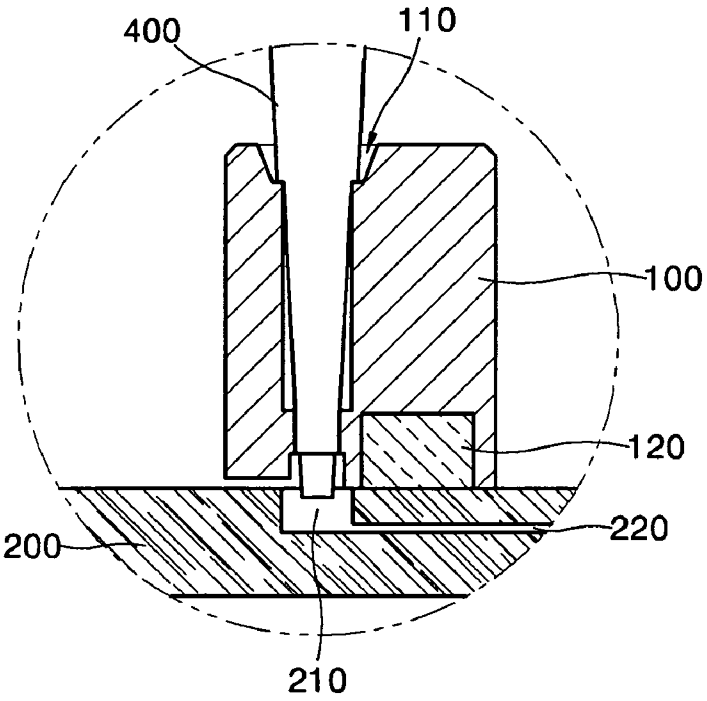
FIG. 5 is a cross-section of the PCR chip unit in FIG. 1 taken along the line 5-5' when a PCR reagent is injected into the PCR chip unit using a pipette and the slider is disposed in the first location.

FIG. 5 is a cross-section of the PCR chip unit in FIG. 1 taken along the line 5-5' when the PCR reagent is injected into the PCR chip unit using a pipette 400 and the slider 100 is disposed in the first location, which is an injection location. As illustrated in FIG. 5, the PCR reagent is injected from the pipette 400 into the reagent inlet 210 of the PCR chip 200 through the injection inlet 110. The injected PCR reagent travels to the chamber 230 via the channel 220. At this time, the pressurizing sealing element 120 on the bottom surface of the slider 100 is not in contact with the reagent inlet 210.

Figure 6:
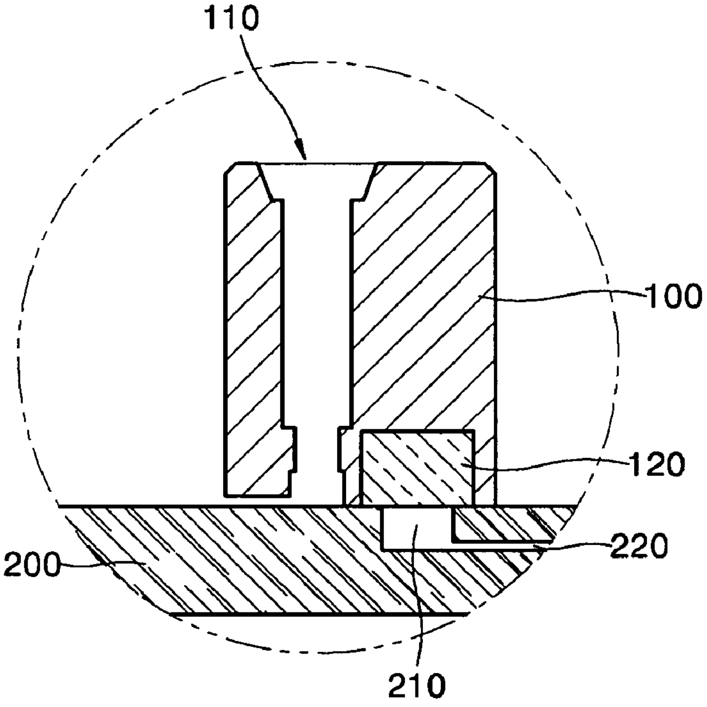
FIG. 6 is a cross-section of the PCR chip unit in FIG. 2 taken along the line 6-6' when the slider is disposed in the second location.

FIG. 6 is a cross-section of the PCR chip unit in FIG. 2 taken along the line 6-6' when the slider 100 is disposed at the second location. As illustrated in FIG. 6, by sliding the slider 100 in the horizontal direction after the PCR reagent is injected, the pressurizing sealing element 120 on the bottom surface of the slider 100 comes in contact with the reagent inlet 210 of the PCR chip 200, thereby sealing the reagent inlet 210. The pressurizing sealing element 120 applies a predetermined pressure in the downward direction such that the pressurizing sealing element 120 is coupled to the PCR chip unit, thereby preventing leakage of the PCR reagent from the reagent inlet 210 during PCR. The pressurizing sealing element 120 can apply a pressure in the downward direction because the pressurizing sealing element 120 is protruded from the bottom surface of the slider 100, which can be explicitly seen when the slider 100 is not coupled to the PCR chip unit.

Figure 7A:
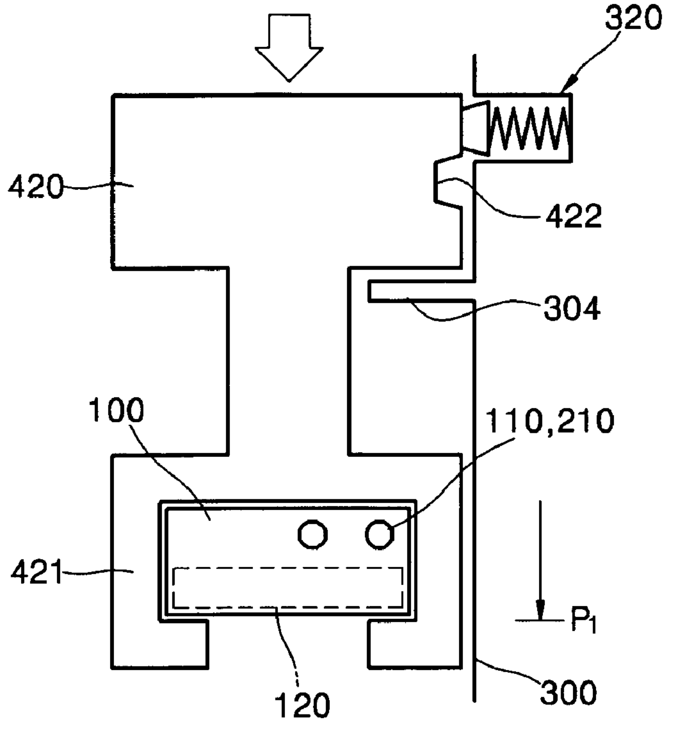
FIGS. 7A and 7B are plan views of a semiautomatic operating device for a microchip according to an embodiment of the present invention.
Figure 7B:
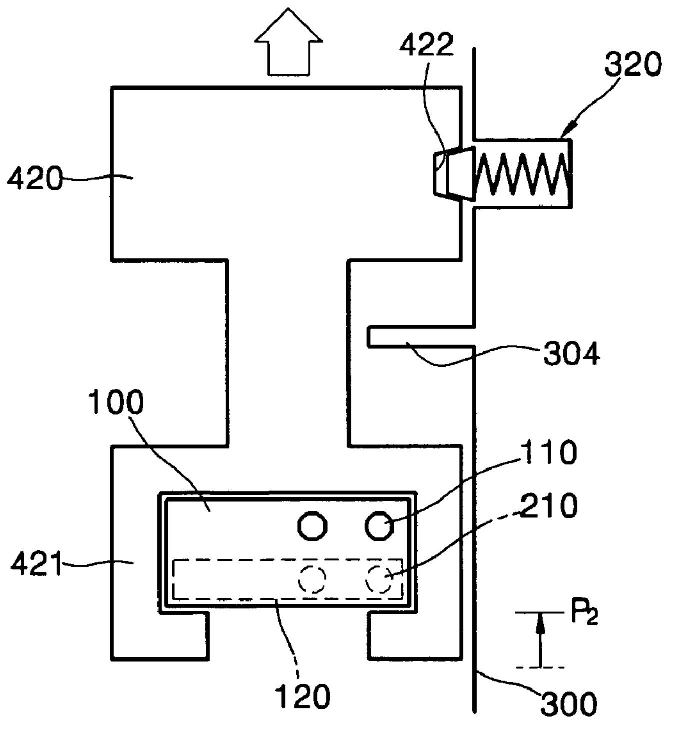

FIGS. 7A and 7B are plan views of a semiautomatic operating device for a microchip according to an embodiment of the present invention. The semiautomatic operating device includes a shuttle 420 which moves parallel to the base 300 after receiving an external force (e.g., pushing or pulling force exerted by a finger) in the direction indicated by an arrow in FIG. 7. A portion 421 of the shuttle 420 is connected to the slider 100 and transmits the external force back and forth to the slider 100. The slider 100 receives the force from the shuttle 420 and reciprocally slides with respect to the base 300 and a microchip (not shown).

The semiautomatic operating device includes a stopper 304 formed as a single body with the base 300 as a first location limiting element which stops the slider 100 from sliding after the slider 100 reaches a first location $P_1$ while sliding in the direction indicated in FIG. 7A. The shuttle 420 slides from top to bottom in FIG. 7A together with the slider 100. Here, when the slider 100 reaches the first location $P_1$, the stopper 304 limits further sliding of the shuttle 420. At the first location $P_1$, the injection inlet 110 of the slider 100 is aligned with the reagent inlet 210 and guides the pipette 400, which injects the PCR reagent, as illustrated in FIG. 5.

The semiautomatic operating device includes second location limiting elements 320 and 422 which stop the slider 100 sliding from the first location $P_1$ after injecting the PCR reagent when the slider 100 reaches a second location $P_2$. The second location limiting element can be an elastic stopper which includes an elastic protrusion 320 formed on the base 300 and a groove 422 formed on one side of the shuttle 420 at a location corresponding to the elastic protrusion 320. In FIG. 7B, the shuttle 420 slides from bottom to top together with the slider 100. Here, when the slider 100 reaches the second location $P_2$, the elastic protrusion 320 enters the groove 422, thereby limiting the sliding of the shuttle 420. At the second location $P_2$, the pressurizing sealing element 120 of the slider 100 covers and pressurizes the reagent inlet 210 and outlet of the microchip, thereby sealing the reagent inlet 210 and outlet, as illustrated in FIG. 6.

Here, the elastic protrusion 320 is forced into a recess in the base 300 when the slider 100 is at the first location $P_1$, and is restored to its original shape and inserted into the groove 422 when the slider 100 is at the second location $P_2$. The location of the elastic protrusion 320 relative to the groove 422 does not change until an external force large enough to retransform the elastic protrusion 320 is applied to the shuttle 420. Therefore, the elastic protrusion 320 and the groove 422 need not be limited as illustrated in FIGS. 7A and 7B. An elastic medium providing a recovery force may be a coil spring, a leaf spring, an elastomer, etc. In addition, the first location limiting element may also be an elastic protrusion and a groove corresponding to the elastic protrusion.

Figure 8A:
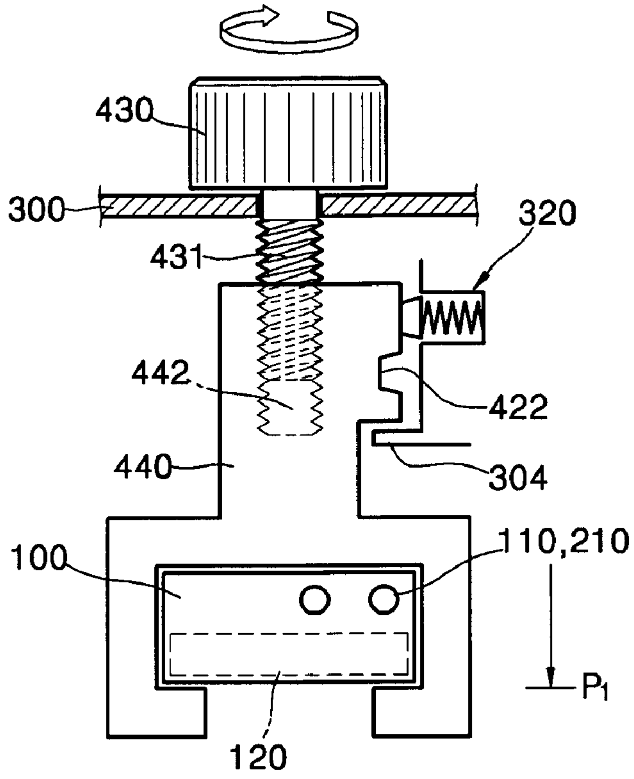
FIGS. 8A and 8B are plan views of a semiautomatic operating device for a microchip according to another embodiment of the present invention.
Figure 8B:
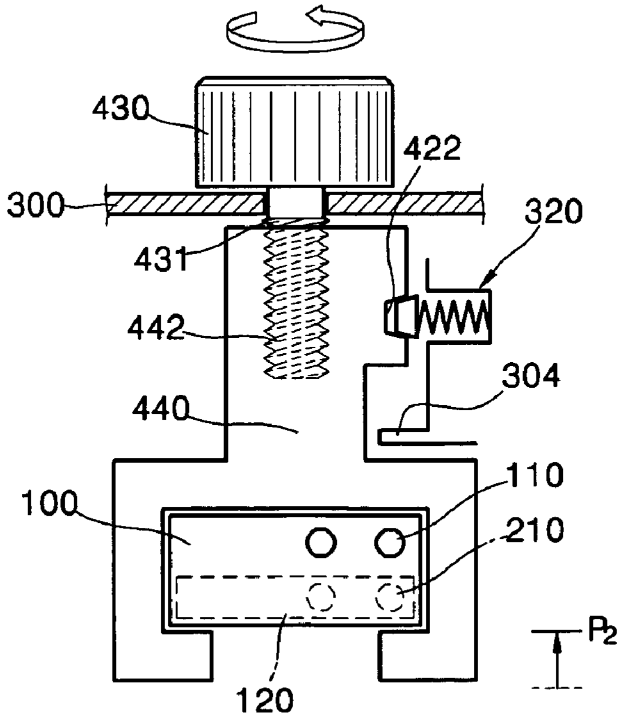

FIGS. 8A and 8B are plan views of a semiautomatic operating device for a microchip according to another embodiment of the present invention. The semiautomatic operating device is installed on one side of the base 300, and includes a rotatable handle 430 connected to a bolt 431 and rotational/linear motion transmitting units 431 and 442 which convert rotation motion of the rotatable handle 430 into linear motion and transmits the linear motion to one end of a shuttle 440. The structure of the rotational/linear motion transmitting unit is limited only to converting the rotation motion at the rotation handle 430 into the linear motion of the shuttle 440, and may be a screw coupling structure, a cylindrical cam structure, a worm gear, or a rack gear.

The semiautomatic operating device according to the present embodiment includes the bolt 431 formed on one end of the rotatable handle 430 and the shuttle 440 having an internal screw 442 formed on one end thereof corresponding to the bolt 431. The location of the slider 100 is fixed at a first location $P_1$ or a second location $P_2$ by limiting the sliding of the shuttle 440 in the same manner as in the previous embodiment, except that first and second location limiting elements can directly limit the rotation of the rotatable handle 430 in the present embodiment.

When providing an automatic operating device, the rotatable handle 430 can be rotated by a motor, and of course, the displacement of the shuttle 440 can be limited by a position control motor.

Figure 9A:
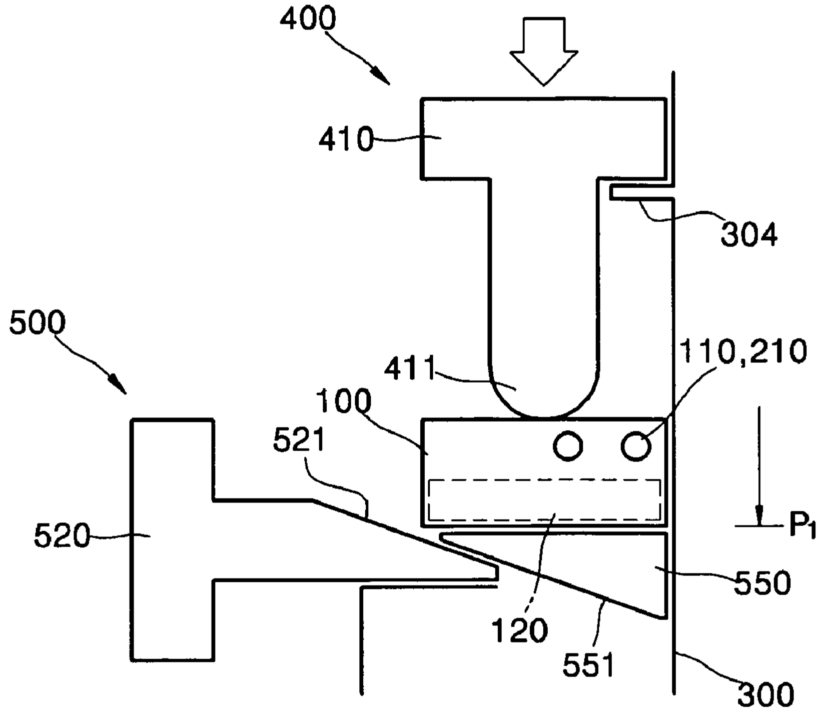
FIGS. 9A and 9B are plan views of a semiautomatic operating device for a microchip according to another embodiment of the present invention.
Figure 9B:
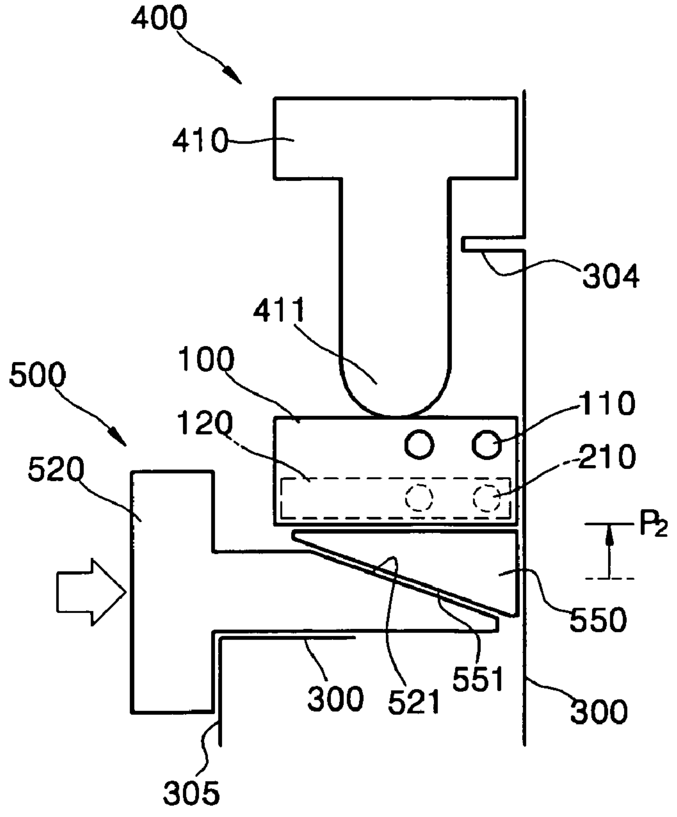

FIGS. 9A and 9B are plan views of a semiautomatic operating device for a microchip according to another embodiment of the present invention. The semiautomatic operating device includes a first moving unit 400, which moves the slider 100 to a first location $P_1$ by pushing the slider 100 in one direction, and a second moving unit 500, which moves the slider 100 from the first location $P_1$ to a second location $P_2$ by pushing the slider 100 in another direction.

Here, the first moving unit includes a first interceptor 410 that is pressed until the slider 100, pushed by one end 411 of the first interceptor 410, reaches the first location $P_1$. The second moving unit includes a second interceptor 520 which is pressed to a predetermined location at a right angle to the direction in which the first interceptor 410 is pressed and a dependent element 550 which moves at a right angle to the direction in which the second interceptor 520 is pressed, indicated by an arrow in FIG. 9B. To obtain this motion, an inclined surface 521 of the second interceptor 520 contacting an inclined surface 551 of the dependent element 550 exerts a force on the inclined surface 551 to move the slider 100 when the second interceptor 520 is pressed. When the second interceptor 520 reaches the predetermined location, the slider 100 reaches the second location $P_2$.

The mechanism of moving the slider 100 using the second interceptor 520 is not limited to that described above. Any cam structure that fixes the slider 100 at the second location $P_2$ by converting the maximum displacement to which the second interceptor 520 is pressed to movement of the slider 100 at a right angle to the displacement is sufficient.

The movement range of the first and second interceptors 410 and 520 can be limited by first and second stoppers 304 and 305 formed on the base 300 as a single body.

Figure 10A:
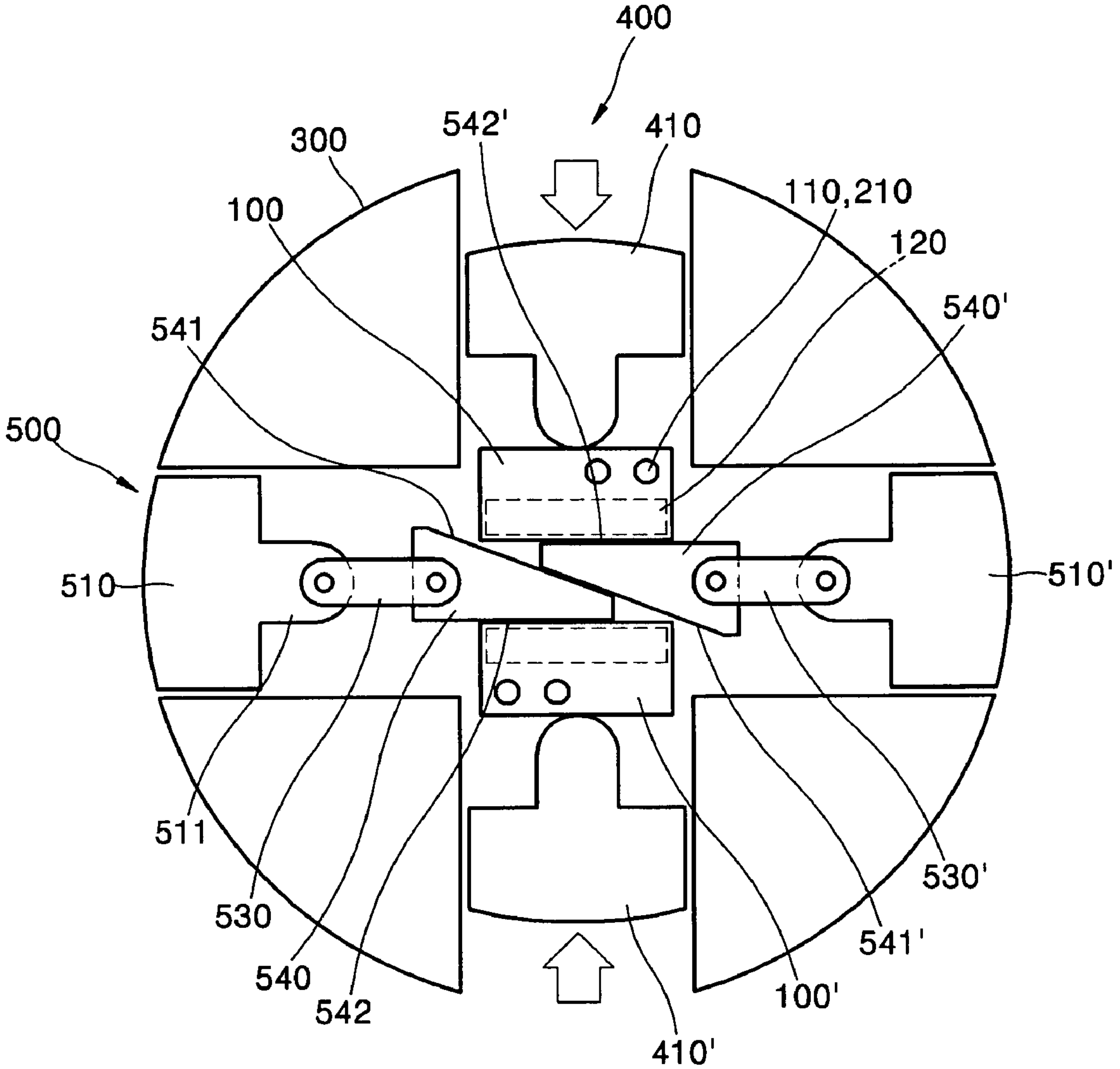
FIGS. 10A and 10B are plan views a semiautomatic operating device for a microchip with a vertical interceptor structure according to an embodiment of the present invention.
Figure 10B:
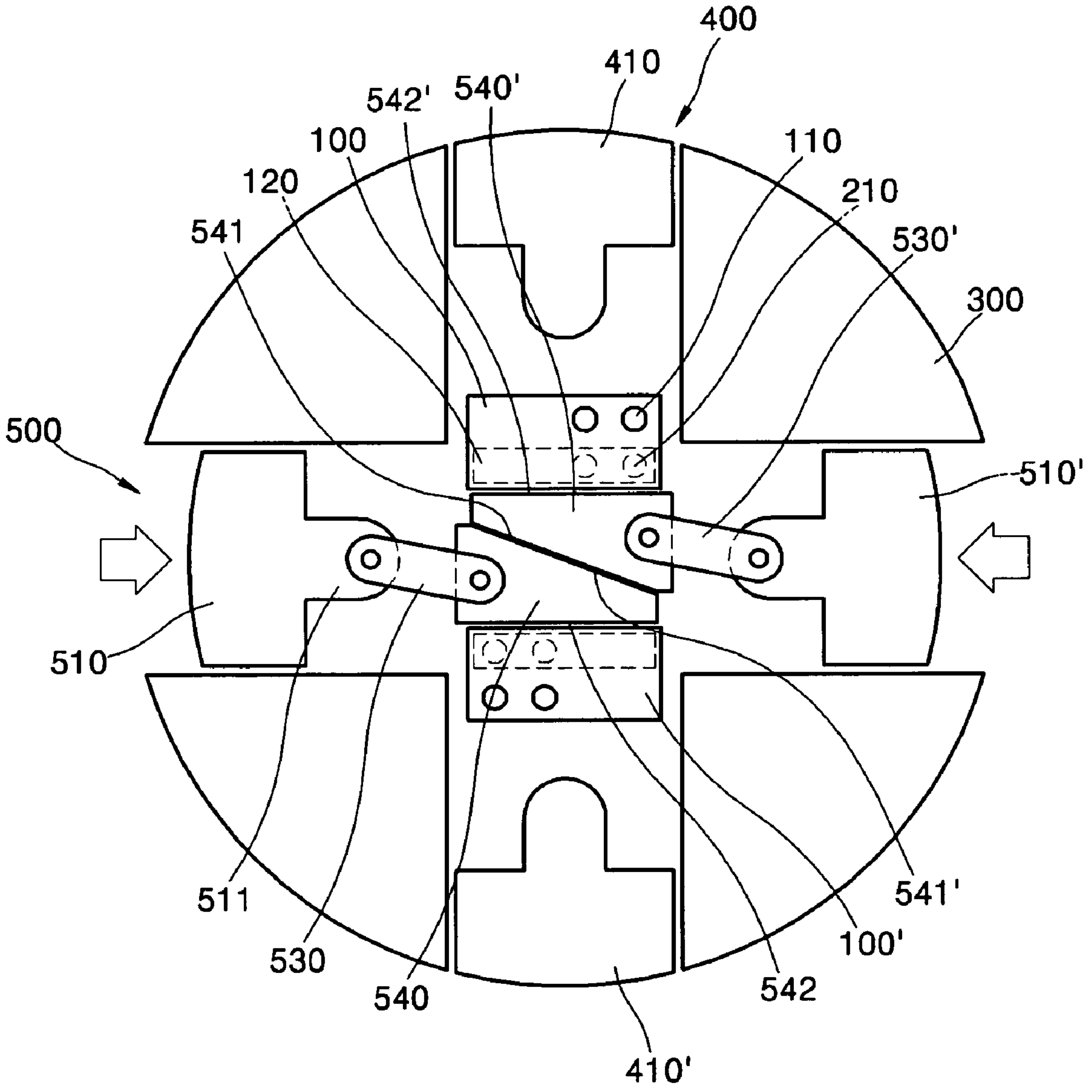

FIGS. 10A and 10B are plan views a semiautomatic operating device of a microchip with a vertical interceptor structure according to an embodiment of the present invention. The semiautomatic operating device includes a base 300, which has an accommodating unit for accommodating the microchip on which a plurality of micro-channels with reagent inlets 210 are formed, and a pair of sliders 100 and 100' that have injection inlets 110 corresponding to each of the reagent inlets 210 and perform reciprocal movement parallel to the base 300 to open and close the reagent inlets 210.

In addition, the semiautomatic operating device includes a pair of first interceptors 410 and 410' to move the pair of sliders 100 and 100' to a first location through a single symmetrical operation and a pair of second interceptors 510 and 510' to move the pair of sliders 100 and 100' from the first location to a second location through a single symmetrical operation.

The first interceptors 410 and 410' face each other and are symmetrically pressed to a predetermined maximum location. As a result, the sliders 100 and 100' can be moved to the first location. The second interceptors 510 and 510' are disposed at right angles to the first interceptors 410 and 410'. The second interceptors 510 and 510 move the sliders 100 and 100' to a second location when pressed to the maximum displacement via a predetermined mechanism. In the predetermined mechanism, front ends of the second interceptors 510 and 510' are respectively connected to a pair of inclined elements 540 and 540' via a pair of connecting loads 530 and 530', and the displacement of the second interceptors 510 and 510' is converted into the displacement of the inclined elements 540 and 540' at right angles to the direction to which the second interceptors 510 and 510' are pressed.

For example, the mechanism may be composed of the pair of inclined elements 540 and 540' and the pair of connecting loads 530 and 530'. Surfaces 542 and 542' of the inclined elements 540 and 540' respectively correspond to surfaces of the sliders 100 and 100' facing each other, and surfaces 541 and 541' of the inclined element 540 opposite the surfaces 542 and 542' are respectively inclined with respect to the surfaces 542 and 542'. The surfaces 541 and 541' face each other between the sliders 100 and 100'. First ends of the connecting loads 530 and 530' are rotatably connected to the inclined elements 540 and 540', respectively, and second ends of the connecting loads 530 and 530' are rotatably connected to the second interceptors 510 and 510', respectively, thereby transmitting the force form the first and second interceptors 510 and 510' to the inclined elements 540 and 540'.

The mechanism through which the sliders 100 and 100' are moved using the second interceptors 510 and 510' is not limited to that described above. Any mechanism which moves the sliders 100 and 100' to the second location $P_2$ by converting the displacement of the second interceptors 510 and 510' into displacement of the sliders 100 and 100' at a right angle to the direction in which the second interceptors 510 and 510' are pressed can be used.

According to the present invention, a semiautomatic operating device for a microchip provides a microchip unit including a slider which guides a pipette for injecting a reaction solution into a reagent inlet of a micro-channel and seals the reagent inlet and outlet of the micro-channel after the reaction solution is injected. Also, regardless of a user's dexterity, the slider can be fixed to a position for an injection mode or a sealing mode through a simple operation of the semiautomatic operation device.

In addition, as described above, by using the semiautomatic operation device which can simply and accurately operate the microchip unit, possibilities of failure due to manual operation are eliminated and the microchip can be further miniaturized and integrated.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A semiautomatic operating device for a microchip on which at least one micro-channel with a reagent inlet is formed, comprising:

a base having an accommodating unit which accommodates the microchip;

a slider with injection inlets corresponding to the reagent inlets that reciprocally move parallel to the base; and a slider moving unit which selectively moves the slider to a first location at which the microchip is opened, after the injection inlet of the slider and the reagent inlet are aligned, and to a second location where the microchip is sealed by a bottom surface of the slider covering the reagent inlet, wherein the slider moving unit comprises:

a shuttle, one end of which receives an external force and the other end of which is equipped with the slider so that the slider can slide back and forth from the first location to the second location when the shuttle slides back and forth with respect to the base by the external force;

a first location limiting element which limits the movement of the shuttle with respect to the base so that the slider stops when the slider reaches the first location; and a second location limiting element which limits the movement of the shuttle with respect to the base so that the slider stops when the slider reaches the second location, wherein at least one of the first location limiting element and the second location limiting element is an elastic stopper comprising a groove formed on one side of the shuttle and the base adjacent to the shuttle, and an elastic element protruding on the other side.

2. The semiautomatic operating device of claim 1, wherein the slider moving unit further comprises:

a rotatable handle rotatably installed on one side of the base; and a rotational/linear motion transmitting unit which converts rotational motion of the rotatable handle into a linear motion and transmits the straight line motion to one end of the shuttle.

3. The semiautomatic operating device of claim 2, wherein the rotational/linear motion transmitting unit has a screw coupling structure which connects one end of the rotatable handle to one end of the shuttle.

4. A semiautomatic operating device of a microchip on which at a plurality of micro-channels with reagent inlets are formed, comprising:

a base which accommodates the microchip;

a pair of sliders with injection inlets corresponding to the reagent inlets that reciprocally move parallel to the base in order to open or close the reagent inlets; and a slider moving unit which selectively moves the pair of sliders to a first location at which the microchip is opened, after the injection inlet of the slider and the reagent inlet are aligned, and to a second location where the microchip is sealed by a bottom surface of the sliders covering the reagent inlet, wherein the slider moving unit comprises:

a first moving unit which slides the pair of sliders to the first location through a symmetrical operation; and a second moving unit which slides the pair of sliders from the first location to the second location through a symmetrical operation, wherein the first moving unit is arranged in a first direction, and the second moving unit is arranged in a second direction, wherein the first direction and the second direction cross each other, wherein the pair of sliders can slide back or forth from the first location to the second location simultaneously when the first moving unit and the second moving unit move back or forth by an external force respectively.

5. The semiautomatic operating device of claim 4, wherein the first moving unit is a pair of first interceptors which are pressed to a predetermined location, and the second moving unit comprises: a pair of second interceptors which are pressed to a predetermined location at a right angle to the direction in which the first interceptor is pressed, and a pair of mechanisms which are connected to front ends of the second interceptors and through which motion of the pair of second interceptors is converted into linear motion in the same direction which the pair of first interceptors move.

6. The semiautomatic operating device of claim 5, wherein the pair of mechanisms comprise:

a pair of inclined elements, first surfaces of which correspond to surfaces of the sliders facing each other, second surfaces of which are inclined with respect to the first surfaces, and the inclined surfaces facing each other between the pair of sliders; and a pair of connecting loads, first ends of which are respectively rotatably connected to the pair of inclined elements, and second ends of which are respectively rotatably connected to the pair of second interceptors.

* * * * *